(12) United States Patent
Dickinson et al.

(10) Patent No.: US 8,986,268 B2
(45) Date of Patent: *Mar. 24, 2015

(54) COVER FOR A FLUID COLLECTION DEVICE

(71) Applicant: Medline Industries, Inc., Mundelein, IL (US)

(72) Inventors: Sarah Dickinson, Chicago, IL (US); Jennifer E. Tomes, Libertyville, IL (US); Robert Lockwood, Libertyville, IL (US)

(73) Assignee: Medline Industries, Inc., Mundelein, IL (US)

( * ) Notice: Subject to any disclaimer, the term of this patent is extended or adjusted under 35 U.S.C. 154(b) by 94 days.

This patent is subject to a terminal disclaimer.

(21) Appl. No.: 13/705,906

(22) Filed: Dec. 5, 2012

(65) Prior Publication Data

US 2013/0094786 A1    Apr. 18, 2013

Related U.S. Application Data

(63) Continuation of application No. 12/897,291, filed on Oct. 4, 2010, now Pat. No. 8,348,914.

(51) Int. Cl.
*A61F 5/44* (2006.01)
*A61M 1/00* (2006.01)
(Continued)

(52) U.S. Cl.
CPC ............... *A61F 5/4404* (2013.01); *B65D 65/08* (2013.01); *A61F 5/445* (2013.01); *A61F 5/449* (2013.01)
USPC .............................. 604/317; 604/327; 383/81

(58) Field of Classification Search
CPC ............................... A61F 5/4404; B65D 65/08

USPC ...................... 150/154; 604/317, 327; 383/81
See application file for complete search history.

(56) References Cited

U.S. PATENT DOCUMENTS

| | | | |
|---|---|---|---|
| 4,122,851 A | 10/1978 | Grossner | |
| 4,606,736 A | 8/1986 | Van De Weghe | |

(Continued)

FOREIGN PATENT DOCUMENTS

| | | |
|---|---|---|
| EP | 0661027 | 12/1994 |
| GB | 2084879 | 4/1982 |
| GB | 2134789 | 8/1984 |

OTHER PUBLICATIONS

Sterigear, "New Urinary Drain Bag Preserves Patient Dignity", FigLeafBag.com, unknown date, downloaded prior to filing date of the present application.

(Continued)

*Primary Examiner* — Sue A Weaver
(74) *Attorney, Agent, or Firm* — David Noskowicz; Philip H. Burrus, IV

(57) ABSTRACT

A cover (100) having one or more openings (106,107) and one or more complementary closure devices (112,113) fits about a fluid drain bag, such as a urinary catheter drain bag (301). The cover (100) can be configured to be both partially transparent and partially opaque. Accordingly, a health services provider (401) can instantly perform rudimentary analysis of the fluid level (401) with a quick glance, yet can perform more in-depth analysis by lifting a front panel (102) at the lower opening (107). The in-depth analysis can be done without removing the cover (100). The cover 100 is also semiopaque, thereby protecting patient dignity by obfuscating the cover's contents.

18 Claims, 5 Drawing Sheets

(51) Int. Cl.
  *B65D 65/08* (2006.01)
  *A61F 5/445* (2006.01)
  *A61F 5/449* (2006.01)

(56) References Cited

U.S. PATENT DOCUMENTS

| | | | |
|---|---|---|---|
| 4,646,467 A | 3/1987 | Morrisroe | |
| 4,705,512 A * | 11/1987 | Faucher | 604/332 |
| 4,826,495 A | 5/1989 | Petersen | |
| 4,874,387 A | 10/1989 | Boone | |
| D315,602 S * | 3/1991 | Howe | D24/110 |
| 5,026,362 A * | 6/1991 | Willett | 604/345 |
| 5,234,420 A | 8/1993 | Horton et al. | |
| 5,248,308 A | 9/1993 | von Emster | |
| 5,415,642 A | 5/1995 | Shepherd | |
| 5,417,676 A | 5/1995 | Watanabe et al. | |
| 5,591,144 A | 1/1997 | Smith et al. | |
| 5,592,946 A * | 1/1997 | Eddy | 600/528 |
| 5,607,412 A | 3/1997 | Brown | |
| 5,759,180 A * | 6/1998 | Myhres | 604/332 |
| 5,865,819 A | 2/1999 | Cisko et al. | |
| 6,186,989 B1 | 2/2001 | Horie | |
| 6,217,376 B1 | 4/2001 | Morita | |
| 6,296,164 B1 | 10/2001 | Russon | |
| D477,873 S * | 7/2003 | Borash et al. | D24/128 |
| 7,001,370 B2 | 2/2006 | Kubalak et al. | |
| 7,691,091 B1 | 4/2010 | Baggett | |
| D618,340 S | 6/2010 | Marshall | |
| 8,348,914 B2 * | 1/2013 | Zyburt et al. | 604/317 |
| 2002/0077609 A1 * | 6/2002 | Johnson | 604/317 |
| 2005/0107758 A1 | 5/2005 | Hogan et al. | |
| 2006/0293631 A1 | 12/2006 | Bolt | |
| 2007/0271672 A1 | 11/2007 | Lentini | |
| 2008/0140033 A1 | 6/2008 | Burgess et al. | |
| 2009/0036874 A1 | 2/2009 | Horowitz et al. | |
| 2009/0062755 A1 | 3/2009 | Burgess et al. | |
| 2009/0234312 A1 | 9/2009 | O'Toole et al. | |
| 2010/0185160 A1 | 7/2010 | Angstrom et al. | |
| 2011/0230863 A1 | 9/2011 | Lentini | |
| 2011/0238024 A1 | 9/2011 | Smith et al. | |

OTHER PUBLICATIONS

Lager, Johan "European Extended Search Report", Application No. 11182982.6; Filed ; REference SJP/P119203EP00; Mailed Jan. 23, 2012.

Weaver, Sue A., "NonFinal Office Action", U.S. Appl. No. 12/897,291, filed Oct. 4, 2010; Mailed Mar. 5, 2012.

Weaver, Sue A., "Notice of Allowance", U.S. Appl. No. 12/897,291, filed Oct. 4, 2010; Mailed Sep. 5, 2012.

Jansson Godoy, Nina "Extended European Search Report", Application No. EP 13168135; Mailed Aug. 9, 2013.

* cited by examiner

COVER FOR A FLUID COLLECTION DEVICE

CROSS REFERENCE TO PRIOR APPLICATIONS

This application is a continuation of U.S. application Ser. No. 12/897,291, filed Oct. 4, 2010, now U.S. Pat. No. 8,348,914, which is incorporated by reference for all purposes.

BACKGROUND

1. Technical Field

This invention relates generally to covers for medical devices, and more particularly to a cover for a fluid collection device.

2. Background Art

Catheters are used to drain fluids from the body. For example, urinary catheters are used to drain a patient's bladder. Catheters are traditionally coupled to drain bags configured to collect the fluid that drains from the catheter. In the case of urinary catheters, the drain bag is generally manufactured from a transparent vinyl material. The transparency allows a medical services provider to see the level of fluid in the bag.

The transparency can raise a patient dignity issue. The visibility of the patient's bodily fluids can be embarrassing. However, traditional covers prevent the necessary fluid visibility needed by the medical services provider.

There is a need for an improved cover.

Figure 1:
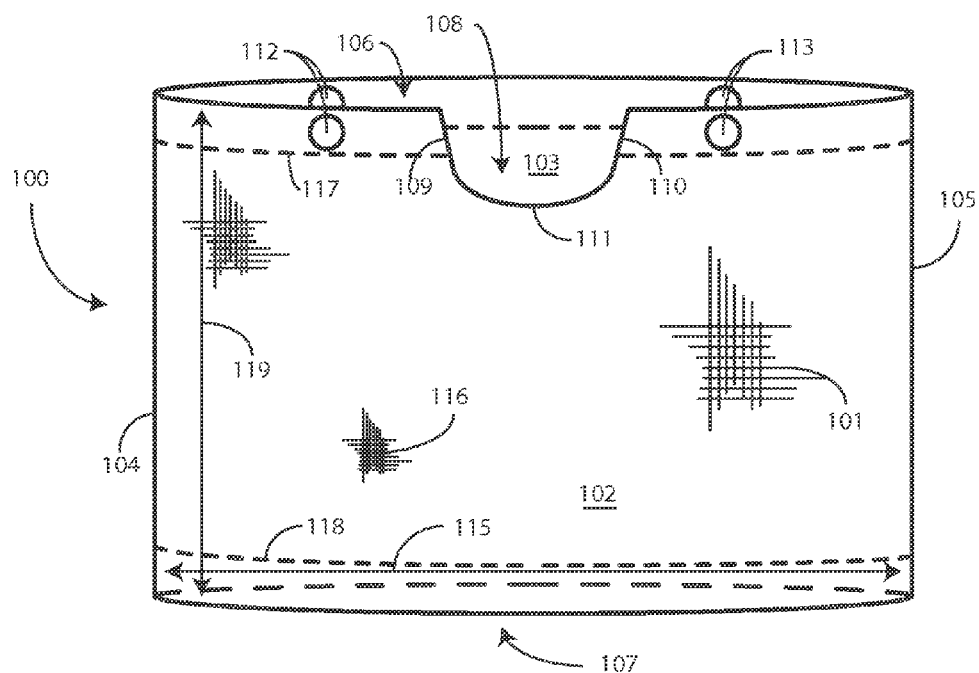
FIG. 1 illustrates one fluid bag cover configured in accordance with embodiments of the invention.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

DETAILED DESCRIPTION OF EMBODIMENTS OF THE INVENTION

Embodiments of the invention are now described in detail. Referring to the drawings, like numbers indicate like parts throughout the views. As used in the description herein and throughout the claims, the following terms take the meanings explicitly associated herein, unless the context clearly dictates otherwise: the meaning of "a," "an," and "the" includes plural reference, the meaning of "in" includes "in" and "on." Relational terms such as first and second, top and bottom, and the like may be used solely to distinguish one entity or action from another entity or action without necessarily requiring or implying any actual such relationship or order between such entities or actions. Also, reference designators shown herein in parenthesis indicate components shown in a figure other than the one in discussion. For example, talking about a device (10) while discussing figure A would refer to an element, 10, shown in figure other than figure A.

Embodiments of the invention are directed to one or more covers for drain bags. In one embodiment, the covers are both semitransparent and semiopaque. These covers are semitransparent enough that a medical services provider, upon close inspection, can identify the level of liquid within a drain bag. However, these covers are semiopaque enough that the covers act as privacy devices by obscuring the identity of the bag or its contents. Accordingly, these covers increase patient dignity.

In one embodiment, where closer observation of the fluid within the bag is required, the cover can be configured with an opening. For example, in one or more embodiments described below, an unsealed opening can be configured in the bottom of the cover. Where this cover is configured to be both semitransparent and semiopaque, a medical services provider can get a rudimentary analysis of the fluid level by looking through the cover. A more thorough analysis can be obtained by raising the cover such that the drain bag passes through the opening. Once the medical services provider has sufficiently analyzed the fluid, gravity will cause the cover to drape back across the drain bag. In one embodiment, the covers are made to be disposable. Accordingly, when a cover becomes soiled, it can simply be thrown away.

Embodiments of the invention offer advantages over prior art bag covers. A first advantage is that of visibility. Illustrating by example, one prior art bag cover is made from an opaque vinyl. While this cover conceals the bag, it does not permit a way for a medical services provider to quickly assess the fluid level within the bag. By contrast, semitransparent and semiopaque embodiments of the present invention allow a medical services provider to quickly and easily discern the amount of fluid within the bag.

A second advantage is concerns the ability to retrofit existing drain bags with covers, as well as the ability to replace covers when they become soiled. Prior art drain bag covers are integrated with the drain bag and cannot be removed or replaced. Embodiments of the present invention are easily applied to a variety of drain bags, and can be quickly removed and replaced. Additionally, the covers of the present invention can be manufactured in a variety of colors so that the color can be selected based upon the application. For instance, a yellow cover may be better suited to concealing certain fluids while a blue cover may be better suited for others.

Figure 2:
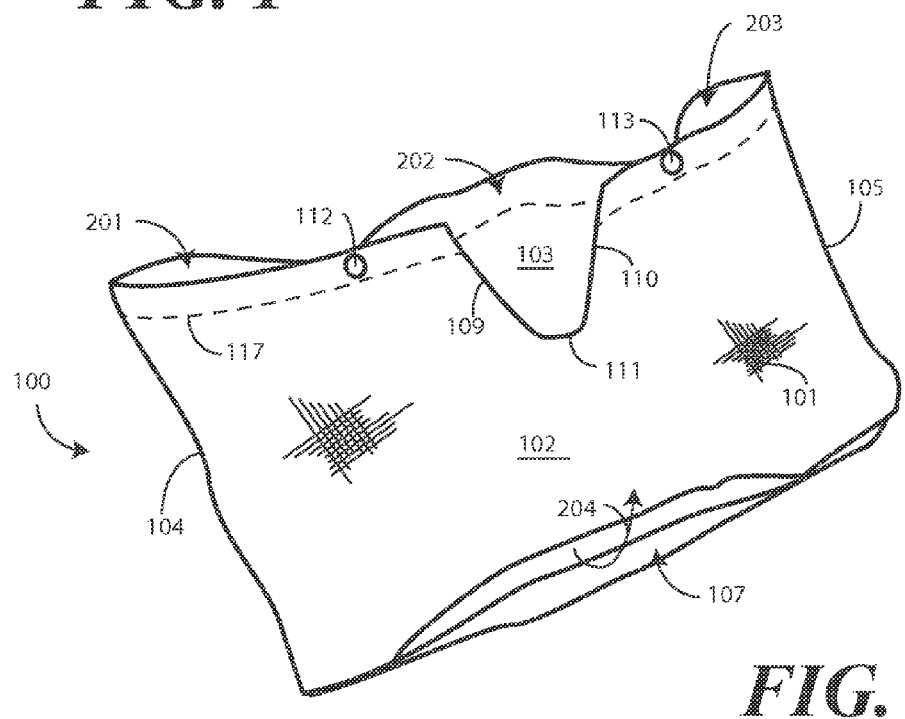
FIG. 2 illustrates one fluid bag cover configured in accordance with embodiments of the invention.

Turning now to FIG. 1, illustrated therein is one embodiment of a cover 100 for a drain bag. FIG. 1 illustrates a front elevation view, while FIG. 2 illustrates a perspective view. The cover 100 of FIG. 1 is well suited for covering catheter drain bags, although it will be clear to those of ordinary skill in the art having the benefit of this disclosure that other drain bags could also be covered with embodiments of the present invention.

In one embodiment, the cover 100 is manufactured from a layer 101 of material. One example of a suitable material is spun bond polypropylene. Experimental testing has shown that a 60-gram spun bond polypropylene works well as the layer 101 of material. Other materials suitable for use with the cover include 40-gram spun bond polypropylene, and a 35-gram tri-layer having a melt-blown layer of polypropylene bonded between two layers of spun bond polypropylene. Spun bond polypropylene is available in a variety of colors, so the color of the cover 100 can be chosen based upon application. In one embodiment, the color of the layer 101 of material is blue.

In the illustrative embodiment of FIG. 1, the layer 101 of material defines a front panel 102, a rear panel 103, a left edge 104, and a right edge 105. In one embodiment, one of the left edge 104 or right edge 105 may include a vertical seam. In another embodiment, a vertical seam may appear either on the front panel 102 or the rear panel 103.

The layer 101 of material defines an upper opening 106 in one embodiment. In the illustrative embodiment of FIGS. 1 and 2, the layer 101 also defines a lower opening 107. The lower opening 107 is optional. Optional stitching 117,118 can be included to provide a hem about the upper opening 106 and/or the lower opening 107.

A concave peninsular opening 108 is centrally disposed along the front panel 102 at the upper opening 106. In one embodiment, the concave peninsular opening 108 is configured as a u-shape. The opening of the concave peninsular opening 108, i.e., the open portion along the upper opening, is at least two inches wide, and in one embodiment is between two and five inches wide. For example, the opening of the concave peninsular opening 108 is three and one-half inches wide.

The sides 109,110 of the concave peninsular opening 108 taper from an opening to a curved base 111. The taper occurs as the concave peninsular opening 108 moves from its opening towards a center of the front panel 102 of the cover 100. While the concave peninsular opening 108 is shown as being a tapered u-shape in FIGS. 1 and 2, it will be clear to those of ordinary skill in the art having the benefit of this disclosure that it can be shaped in other ways as well. For example, it can be squared, triangular, rectangular, parabolic, and so forth.

In one embodiment, the depth of the concave peninsular opening 108, i.e., the distance between the upper opening 106 and the curved base 111 is at least two inches, and in one embodiment is between two and four inches wide. For example, the depth can be three and one-half inches. As will be shown in FIG. 4 below, the concave peninsular opening 108 provides space for accessories used in conjunction with some drain bags.

Two complementary closure devices 112,113 are disposed along the upper opening 106. The two complementary closure devices 112,113 are configured to retain the front panel 102 and the rear panel 103 together by closing the upper opening 106 in at least two locations. While two complementary closure devices 112,113 are shown, embodiments of the invention contemplate that more than two closure devices can be used as well.

In the illustrative embodiment of FIGS. 1 and 2, the complementary closure devices 112,113 are snaps. However, other closure devices can be used as well. In another embodiment, the complementary closure devices 112,113 are configured as hook and loop fasteners. One example of a hook and loop fastener is Velcro®. In another embodiment, the complementary closure devices 112,113 can be configured as straps that extend from the rear panel 103 across the upper opening 106 to the front panel and close with buttons, snaps, hooks, latches, or hook and loop fasteners. Other closure devices will be readily apparent to those of ordinary skill in the art having the benefit of this disclosure. In one or more embodiments, the complementary closure devices 112,113 are configured for repeated use, such that the upper opening 106 can be opened or closed multiple times. In yet another embodiment, the complementary closure devices 112,113 could be removed. In their place, one or more strips of elastic material may be placed within the hem formed by seam 117. This elastic material can be configured to cinch around a drain bag, thereby serving as another form of closure device.

In this illustrative embodiment, a first complementary closure device 112 is situated to the left of the concave peninsular opening 108. A second complementary closure device 113 is situated to the right of the concave peninsular opening 108. In one embodiment, the first complementary closure device 112 and the second complementary closure device 113 are equidistant from the concave peninsular opening 108. As shown in FIG. 2, in this illustrative embodiment when the complementary closure devices 112,113 are engaged, the upper opening 106 defines a plurality of upper openings 201,202,203. Since two complementary closure devices 112,113 are used, the plurality of upper openings 201,202,203 comprises three upper openings.

As shown in FIG. 2, in this particular embodiment the lower opening 107 can be partially folded 204 so as to expand the lower opening 107. When the cover 100 is disposed about a drain bag, a medical services provider can fold 204 the front panel 102 up to more closely examine the fluid contents of the drain bag. This will be shown in more detail in the discussion of FIG. 4 below.

The dimensions of the cover 100 can vary based upon application. In one embodiment configured for a urinary catheter bag, the width 114 of the front panel 102 and rear panel 103 is between ten and twelve inches. In one embodiment, the width 114 is eleven inches. In one embodiment, the length 115 of the front panel 102 and rear panel 103 is between eleven and thirteen inches. In one embodiment, the length 115 is twelve and one-half inches. These dimensions are illustrative only, as others may also be used.

Using the dimensions of the preceding paragraph, experimental testing has yielded a few other dimensions of note. For example, in one embodiment the distance between the first complementary closure device 112 and the left edge is three and one-half inches. Similarly, the distance between the second complementary closure device 113 and the right edge 105 is three and one-half inches. Where the concave peninsular opening 108 is centered along the front panel 102, the opening can begin about four and one-half inches from the right edge 105 and left edge 104, respectively. Experimental testing has shown that these dimensions provide essentially a universal cover 100 that fits urinary catheter drain bags that are readily available from a variety of manufacturers, even though these various drain bags may be manufactured with different dimensions.

In one embodiment, the layer 101 of material is configured to be both semitransparent and semiopaque. The layer 101 is semitransparent enough so that a medical services provider can at least partially see through the layer 101 to get a rudimentary analysis of, for example, fluid levels within a drain bag disposed within the cover. However, the layer 101 is semiopaque enough so that the patient's privacy is protected in that the identity of the fluid or potentially the identity of the type of drain bag is obfuscated. Experimental testing has shown that 60-gram spun bond polypropylene works well in that the weave 116 of the material provides sufficient semi-transparency and semiopaqueness. While other materials can be used, experimental testing has shown that some materials, such as 35-gram trilayers of melt-blown layer of polypropylene bonded between two layers of spun bond polypropylene may not provide sufficient transparency for all applications. It is well to note that the color of the layer 101 of material can also affect the transparency or opacity. Experimental testing has shown that blue spun bond polypropylene with a weight above 20 grams working well in urinary catheter drain bag applications, with 60-gram blue spun bond polypropylene working particularly well.

Figure 3:
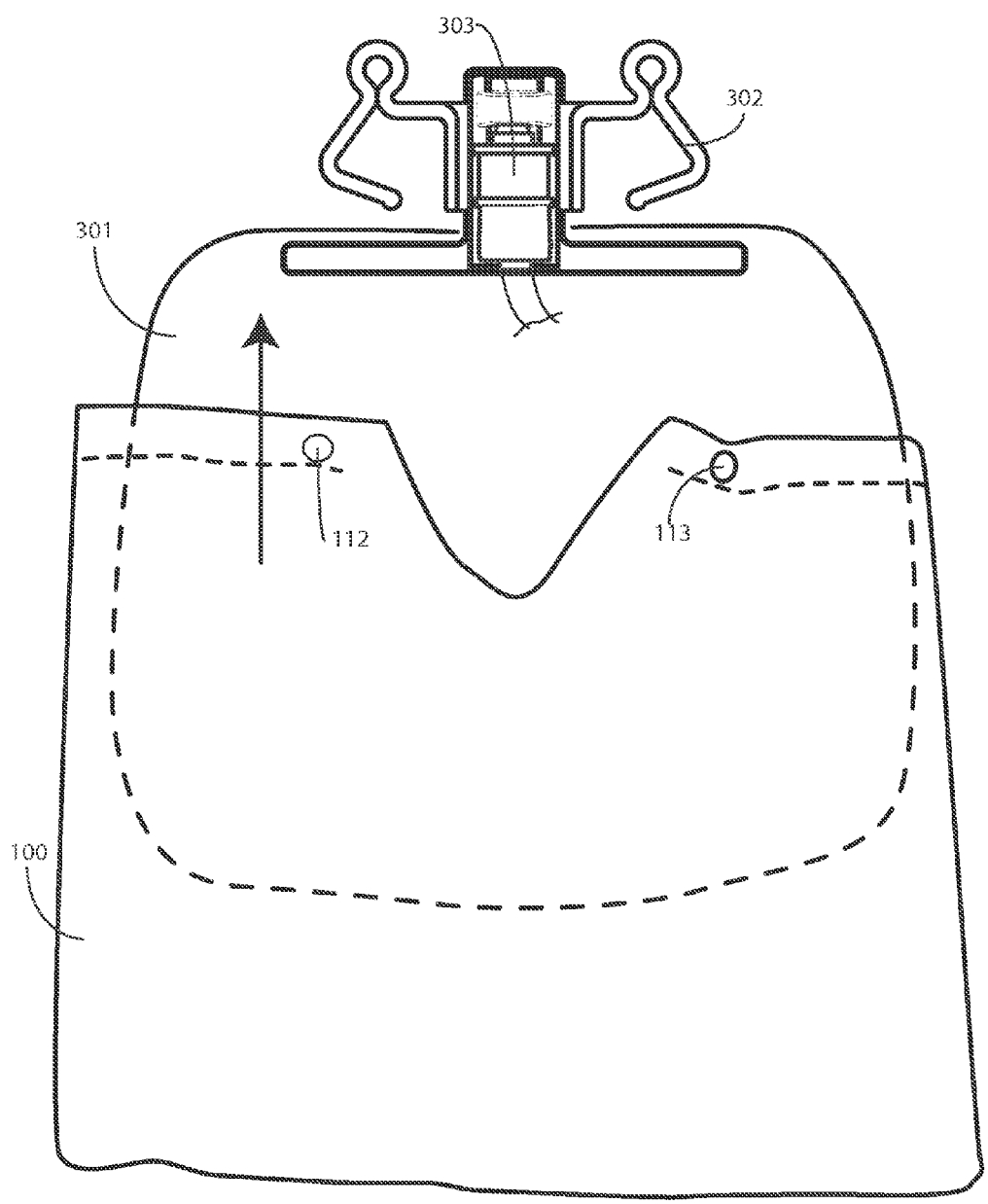
FIG. 3 illustrates a drain bag being inserted into a cover in accordance with embodiments of the invention.

Turning now to FIG. 3, illustrated therein is the cover 100 of FIG. 1 being placed about a urinary catheter drain bag 301. The complementary closure devices 112,113 are disengaged, thereby leaving the upper opening (106) fully open. The urinary catheter drain bag 301 can then be slipped into the upper opening (106). Once in place, the complementary closure devices 112,113 can be engaged as shown in FIG. 4.

As shown in the illustrative embodiment of FIG. 3, the urinary catheter drain bag 301 is equipped with a hanger 302. The hanger 302 can be used to attach the urinary catheter drain bag 301 to a variety of devices, including drain bag stands and hospital or nursing home beds. Attached to the hanger 302 is an anti-reflux valve 303. This device enables the medical services provider to readily see fluids going into the bag. The device also prevents fluid displacement in the opposite direction.

Figure 4:
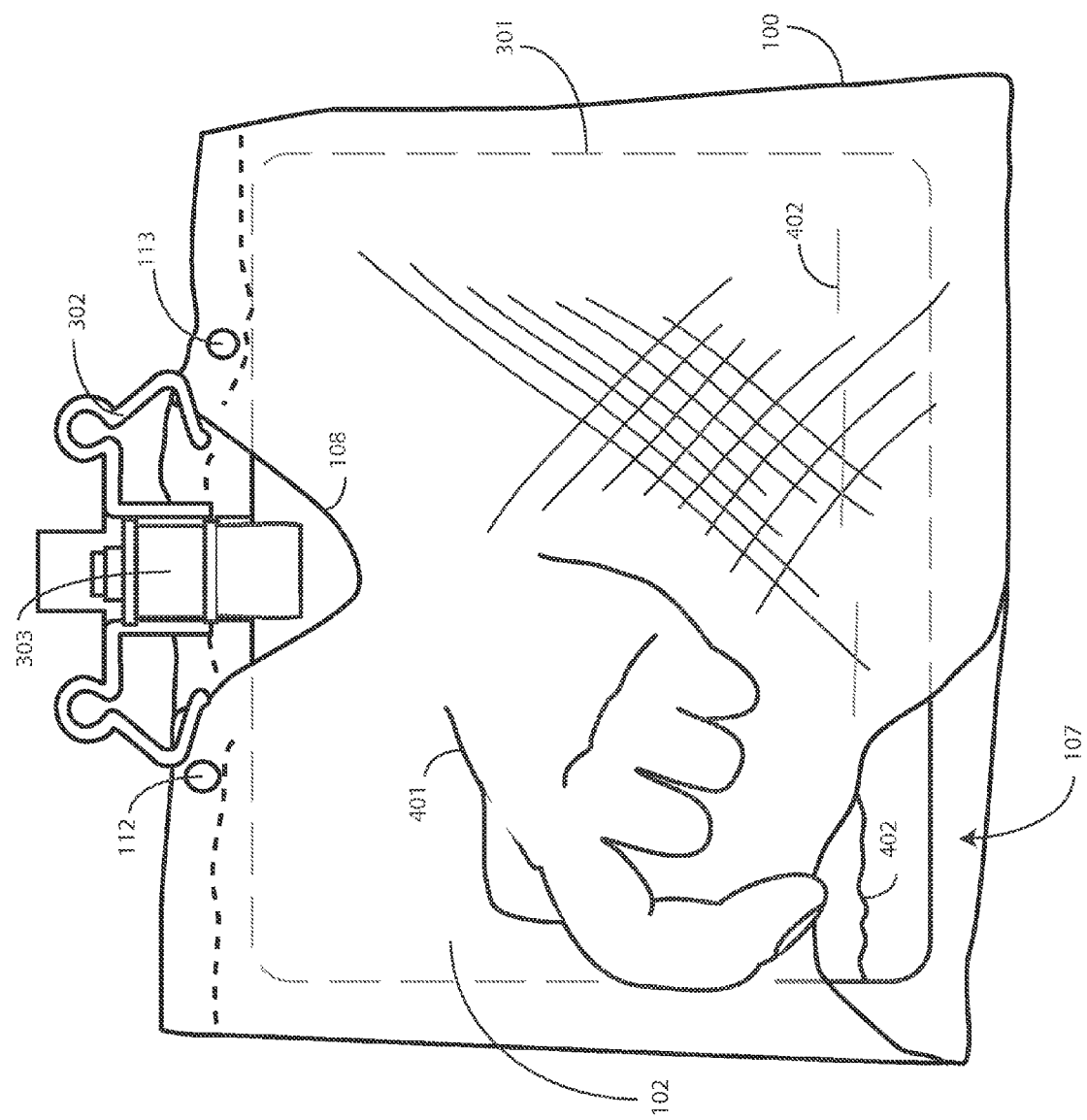
FIG. 4 illustrates one fluid bag cover placed about a drain bag in accordance with embodiments of the invention.

Turning now to FIG. 4, when the urinary catheter drain bag 301 is fully placed within the cover 100 and the complementary closure devices 112,113 are engaged, the anti-reflux valve 303 sits within the concave peninsular opening 108. The complementary closure devices 112,113 are situated on either side of the hanger 302, thereby preventing the cover 100 from falling off the urinary catheter drain bag 301.

The cover 100 of FIG. 4 is both partially transparent and partially opaque. Accordingly, the outline of the urinary catheter drain bag 301 is partially obfuscated, as indicated by the lighter, dashed lines. However, the partial transparency allows a health services provider 401 to obtain a rudimentary analysis of the fluid level 402 within the urinary catheter drain bag 301.

In the illustrative embodiment of FIG. 4, the cover 100 is equipped with the optional lower opening 107. Accordingly, when the health services provider 401 wants to obtain a more in-depth analysis of the fluid level 402, the health services provider 401 may simply pull back the lower opening 107, thereby revealing the urinary catheter drain bag 301. By releasing the edge of the lower opening, gravity will cause the front panel 102 to fall back across and cover the urinary catheter drain bag 301.

Embodiments of the cover offer several advantages over prior art solutions. A first advantage is that the health services provider 401 can instantly perform rudimentary analyses of the fluid level 401 with a quick glance, yet can perform more in-depth analyses by lifting the front panel 102 at the lower opening 107. The in-depth analysis can be done without removing the cover 100. However, despite being semitransparent, the cover 100 is also semiopaque, thereby protecting patient dignity by obfuscating the cover's contents. Another advantage is that the cover 100 can be configured to be detachable from the urinary catheter drain bag 301 and disposable. This allows the health services provide 401 to dispose/replace the cover 100 if it becomes dirty or contaminated.

Figure 5:
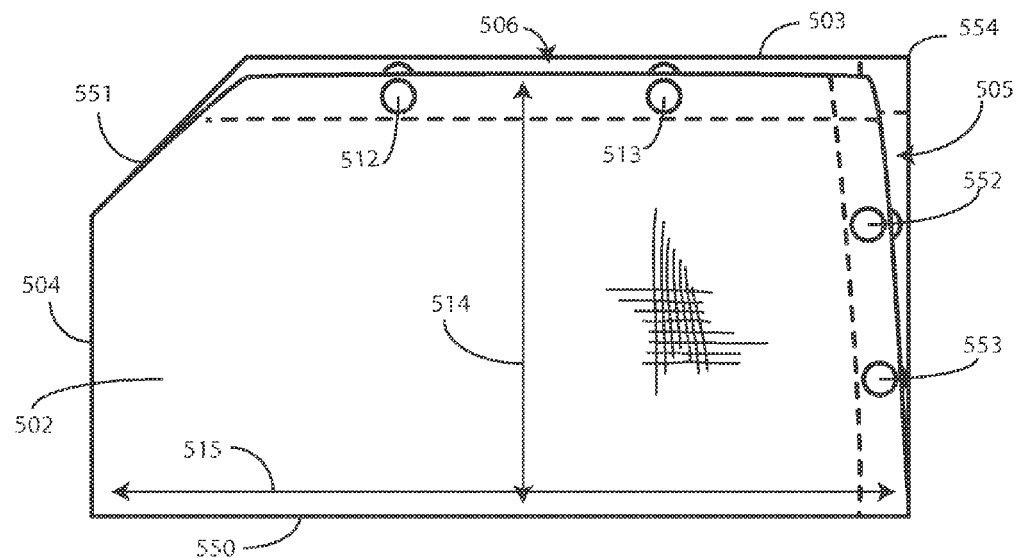
FIG. 5 illustrates another fluid bag cover configured in accordance with embodiments of the invention.

Turning now to FIG. 5, illustrated therein is an alternate embodiment of a cover 500 configured in accordance with embodiments of the invention. The cover 500 of FIG. 5 is designed to accommodate a low-bed catheter drain bag.

As with FIGS. 1 and 2, the cover 500 of FIG. 5 includes a layer 501 of material defining a front panel 502, rear panel 503, and a left edge 504. Rather than having a bottom opening (107), the cover 500 of FIG. 5 includes a bottom edge 550 that is closed. A right edge opening 505 is provided, as is an upper opening 506. A corner opening 551 runs from the left edge 504 to the upper opening 506. In one embodiment, the corner opening 551 is non-orthogonal with both the left edge 504 and the upper opening 506. For example, the corner opening 551 in one embodiment is oriented at about forty-five degrees.

In the embodiment of FIG. 5, at least four complementary closure devices 512,513,552,553 are disposed along the openings, with at least two complementary closure devices 512,513 disposed along the upper opening 506 and at least two complementary closure devices 552,553 disposed along the right edge opening 505. As with the embodiment of FIGS. 1 and 2, the four complementary closure devices can be snaps, hook and loop closures, or other devices. Further, more complementary closure devices can be included, and one complementary closure device can be substituted for the two complementary closure devices 552,553 disposed along the right edge opening 505. The four complementary closure devices 512,513,552,553 are configured to retain the front panel 502 and rear panel 503 together to close the upper opening 506 and the right edge opening 505 in at least two locations, respectively.

As is evident from comparing FIG. 5 to FIG. 1, the cover 500 of FIG. 5 includes different dimensions, each of which have been obtained from experimental testing. For instance, in one embodiment the front panel 502 and the back panel 503 each have a width 514 of between eight and ten inches. In one embodiment, the width 514 is nine inches. Similarly, in one embodiment the front panel 502 and back panel 503 have a length 515 of between sixteen and eighteen inches. In one embodiment, the length 515 is seventeen inches.

Other dimensions are worthy of note. In one embodiment, the left edge 504 is between five and six inches in length. In one embodiment, the left edge is five and one-half inches in length. In one or more embodiments, the upper opening 506 is between twelve and fourteen inches in length, and is thirteen and a quarter inches in one embodiment. The first complementary enclosure device 512 is five and one half inches from the secondary complementary closure device 513 in one embodiment, with the first complementary closure device being situated about two and one half inches from the corner opening 551. Along the right edge opening 505, complementary closure device 552 is three inches from complementary closure device 553 in one embodiment, with complementary closure device 552 being situated three inches from corner 554.

As with the cover (100) of FIGS. 1 and 2, in one embodiment the cover 500 can be configured to be both semitransparent and semiopaque. For example, in one embodiment the layer 501 of material comprises 60-gram spun bond polypropylene. The weight of this material creates enough thickness to obfuscate and disguise contents disposed within the cover 500, but is light enough to allow a fluid level to be seen without removing the cover 500. In one embodiment, the cover 500 is blue. Accordingly, the advantages offered by the cover (100) of FIGS. 1 and 2 are similarly offered by the cover 500 of FIG. 5.

Figure 6:
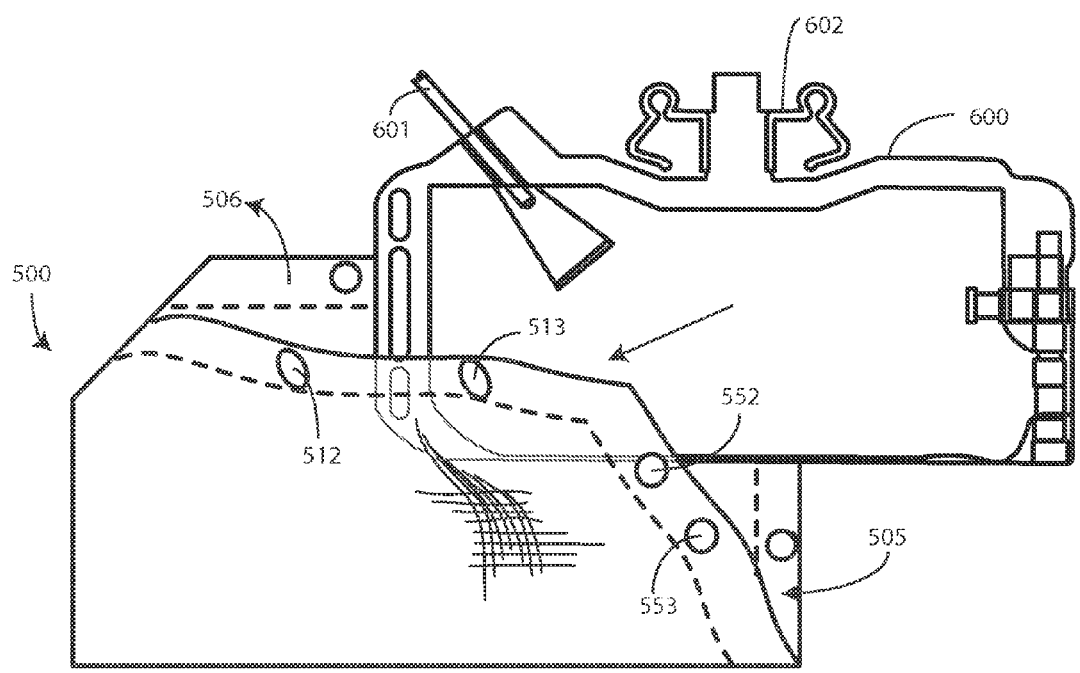
FIG. 6 illustrates another drain bag being inserted into a cover in accordance with embodiments of the invention.

Turning now to FIG. 6, illustrated therein is the cover 500 of FIG. 5 being placed about a low-bed urinary catheter drain bag 600. Low-bed urinary catheter drain bags are illustrated and described in commonly assigned, co-pending U.S. patent application Ser. No. 11/634,714, entitled "Fluid Collection System and Methods of Using Same," filed Dec. 6, 2006, which is incorporated herein by reference. The complementary closure devices 512,513,552,553 are disengaged, thereby leaving the upper opening 506 and right edge opening 505 fully open. The low-bed urinary catheter drain bag 600 can then be slipped into the combined opening. Once in place, the complementary closure devices 512,513,552,553 can be engaged as shown in FIG. 7.

As shown in the illustrative embodiment of FIG. 6, the low-bed urinary catheter drain bag 600 includes a coupler 601 for connection to a catheter. Additionally, a hanger 602 can be used to attach the low-bed urinary catheter drain bag 600 to a variety of devices, including drain bag stands and low hospital or nursing home beds.

Figure 7:
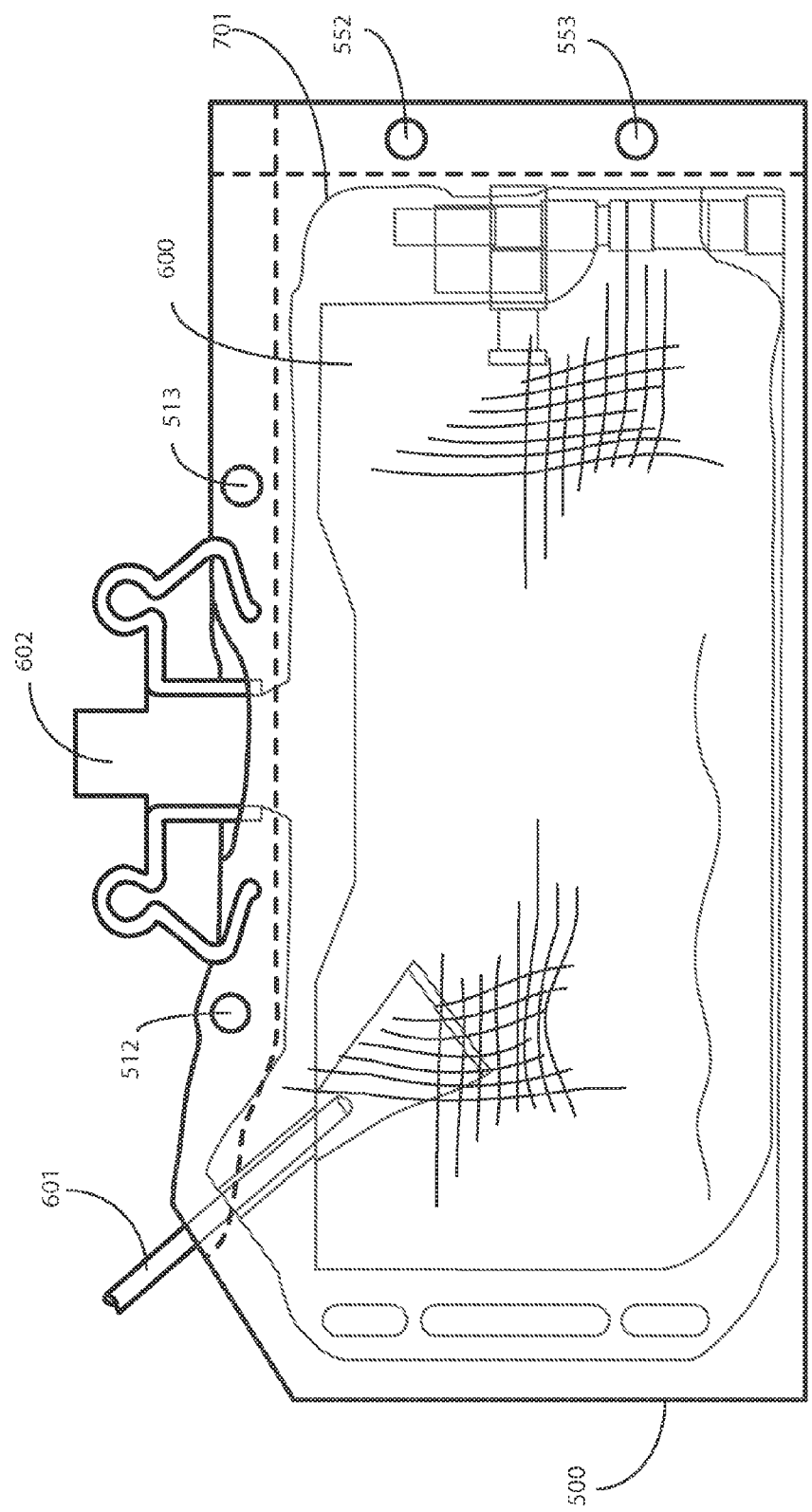
FIG. 7 illustrates another fluid bag cover placed about another drain bag in accordance with embodiments of the invention.

Turning now to FIG. 7, when the low-bed urinary catheter drain bag 600 is fully placed within the cover 500 and the complementary closure devices 512,513,552,553 are engaged, the connector 601 fits within the corner opening 551. Complementary closure devices 512,513 are situated on either side of the hanger 602, thereby preventing the cover 500 from falling off the low-bed urinary catheter drain bag 600.

Where the cover 500 is both partially transparent and partially opaque, the outline 701 of the low-bed urinary catheter drain bag 600 is partially obfuscated. However, the partial transparency allows a health services provider to obtain a rudimentary analysis of the fluid level within the low-bed urinary catheter drain bag 600.

In the foregoing specification, specific embodiments of the present invention have been described. However, one of ordinary skill in the art appreciates that various modifications and changes can be made without departing from the scope of the present invention as set forth in the claims below. Thus, while preferred embodiments of the invention have been illustrated and described, it is clear that the invention is not so limited. Numerous modifications, changes, variations, substitutions, and equivalents will occur to those skilled in the art without departing from the spirit and scope of the present invention as defined by the following claims. Accordingly, the specification and figures are to be regarded in an illustrative rather than a restrictive sense, and all such modifications are intended to be included within the scope of present invention. The benefits, advantages, solutions to problems, and any element(s) that may cause any benefit, advantage, or solution to occur or become more pronounced are not to be construed as a critical, required, or essential features or elements of any or all the claims.

What is claimed is:

1. A cover for a catheter drain bag, comprising:
    a layer of material defining a front panel, rear panel, a left edge, and a right edge, wherein the layer of material further defines a lower opening and an upper opening, and wherein the front panel defines a concave peninsular opening that is centrally disposed at the upper opening of the front panel; and
    at least one complementary closure device disposed along the upper opening and being configured to retain the front panel and rear panel together to close the upper opening in at least one location, wherein the at least one complementary closure device is situated one of left of the concave peninsular opening or right of the concave peninsular opening.

2. The cover of claim 1, wherein the at least one complementary closure device is configured such that the upper opening defines a plurality of upper openings when the at least one complementary closure device is engaged.

3. The cover of claim 2, wherein the at least one complementary closure device comprises a snap.

4. The cover of claim 1, wherein the concave peninsular opening comprises a u-shape that tapers from an opening to a base toward a center of the cover.

5. The cover of claim 1, wherein the concave peninsular opening has a depth of at least two inches.

6. The cover of claim 1, wherein the concave peninsular opening has a mouth that is at least two inches wide.

7. The cover of claim 1, wherein the front panel and the rear panel each have a width between ten and twelve inches and a length of between eleven and thirteen inches.

8. The cover of claim 1, wherein the layer of material is both semitransparent and semiopaque.

9. The cover of claim 8, wherein the layer of material comprises spun bond polypropylene.

10. The cover of claim 9, wherein the layer of material is blue.

11. A cover for a drain bag, comprising:
    a layer of material defining a front panel, rear panel, a left edge, and a bottom edge, wherein the layer of material further defines an upper opening, a right edge opening, and a corner opening running from the left edge to the upper opening, wherein the corner opening is non-orthogonal with both the left edge and the upper opening; and
    at least two complementary closure devices, with at least a first one complementary closure device disposed along the upper opening and at least a second complementary closure device disposed along the right edge opening, the at least two complementary closure devices being configured to retain the front panel and rear panel together to close the upper opening and the right edge opening in at least two locations.

12. The cover of claim 11, wherein the front panel and the rear panel each have a width between eight and ten inches and a length of between sixteen and eighteen inches.

13. The cover of claim 12, wherein the left edge is between five and six inches in length and the upper opening is between twelve and fourteen inches in length.

14. The cover of claim 13, wherein a complementary closure device is situated about three inches from an intersection of the upper opening and the right edge opening.

15. The cover of claim 13, wherein a complementary closure device is situated about two and one half inches from the corner opening.

16. The cover of claim 13, wherein the layer of material is both semitransparent and semiopaque.

17. The cover of claim 16, wherein the layer of material comprises spun bond polypropylene.

18. The cover of claim 17, wherein the layer of material is blue.

* * * * *